United States Patent
Tsutsui et al.

(12)

(10) Patent No.: US 6,414,208 B1
(45) Date of Patent: Jul. 2, 2002

(54) PROCESS FOR PRODUCING DIMETYLNAPHTHALENE AND ALKYLNAPHTHALENE WITH METHALLOSILICATE CATALYST

(75) Inventors: Toshio Tsutsui; Osamu Kubota; Masataka Wakabayashi, all of Chiba-Ken; Tomoyuki Inui, Kyoto-Fu; Shu Bin Pu, Hyogo-Ken, all of (JP)

(73) Assignee: Fuji Oil Company, Ltd., Tokyo-To (JP)

( * ) Notice: Subject to any disclaimer, the term of this patent is extended or adjusted under 35 U.S.C. 154(b) by 0 days.

(21) Appl. No.: 09/540,541

(22) Filed: Mar. 31, 2000

(30) Foreign Application Priority Data

Mar. 31, 1999 (JP) ............................................. 11-093355
Apr. 1, 1999 (JP) ............................................. 11-095170

(51) Int. Cl.⁷ ................................................. C07C 5/22
(52) U.S. Cl. ........................ 585/481; 585/480; 585/906
(58) Field of Search ................................ 585/480, 481, 585/906; 502/85, 86

(56) References Cited

U.S. PATENT DOCUMENTS 4,520,221 A * 5/1985 Hsia Chen .................. 585/517

\* cited by examiner

*Primary Examiner*—Thuan D. Dang
(74) *Attorney, Agent, or Firm*—Wenderoth, Lind & Ponack LLP

(57) ABSTRACT

A process for producing 2,6-dimethylnaphthalene by subjecting 2,7-dimethylnaphthalene to an isomerization reaction, wherein the isomerization reaction is carried out by the use of a metallosilicate catalyst that comprises a metallosilicate having a main cavity defined by a ten-oxygen-membered ring, that is in the form of aggregates of fine crystals of the metallosilicate, the external surface area of the aggregate as calculated from t-plot analysis made in the nitrogen adsorption method being 25 $m^2/g$ or more, and that has been treated to inactivate acid centers present on the external surfaces of the fine crystals until the rate constant basic value N becomes 0.5 or less.

3 Claims, No Drawings

PROCESS FOR PRODUCING DIMETYLNAPHTHALENE AND ALKYLNAPHTHALENE WITH METALLOSILICATE CATALYST

BACKGROUND OF THE INVENTION

1. Field of the Invention

The present invention relates to a process for producing petrochemicals, using as a metallosilicate catalyst whose main cavity is defined by a ten-oxygen-membered ring.

2. Background Art

Since metallosilicates—"metallosilicates" is herein a general term for aluminosilicates and their analogues in which aluminum atoms contained in the aluminosilicate framework are replaced with other metals—have solid acidity. For that reason, they have conventionally been used as catalysts for hydrocarbon conversion reactions such as catalytic cracking, hydrocracking, disproportionation and isomerization, and various chemical reactions such as chemical synthesis reactions. A metallosilicate is present as a crystal having stereoregular structure in which oxygen atom is shared by a $SiO_4$ tetrahedron and an $MO_4$ (M is Al or any other metal atom) tetrahedron to form a three-dimensional network. In such a crystal, a ring composed of Si, O and M atoms, characteristic of the above linkage forms a cavity.

Metallosilicates show various solid acidities depending upon, for example, the type of metallosilicate and the coexisting cation, and have their own characteristic cavities. Moreover, the particle diameters of metallosilicates are controllable, and various modifications of metallosilicates are possible. Therefore, metallosilicates suitable as catalysts for specific chemical reactions have respectively been developed and used. For instance, among metallosilicates in which M is aluminum, that is, aluminosilicates, X- or Y-type aluminosilicate called faujasite is used, for example, as a catalyst for catalytic cracking or hydrocracking in petroleum refining; mordenite is used, for example, as a disproportionation or isomerization catalyst; and ZSM-5 is used as a catalyst for the synthesis of gasoline from methanol, or for various chemical synthesis reactions. Further, metallosilicates in which M is a metal atom other than aluminum are used as catalysts, for example, for the aromatization of light naphtha.

On the other hand, there is a demand for zeolite catalysts that show great specificity and high selectivity in specific chemical reactions. 2,6-Dimethylnaphthalene, for instance, can be produced by the isomerization reaction of a dimethylnaphthalene. It has been known that, although the isomerization of a dimethylnaphthalene, where methyl group is transferred from the α-position to the adjacent β-position and vice versa, can readily be attained, it is difficult to conduct isomerization of other types (Fries rule). It has therefore been difficult to isomerize a dimethylnaphthalene included in one of the following four groups of (1)–(4) to one included in any of the other groups:

(1) the group of 2,6-dimethylnaphthalene: 2,6-dimethylnaphthalene, 1,6-dimethylnaphthalene and 1,5-dimethylnaphthalene;

(2) the group of 2,7-dimethylnaphthalene: 2,7-dimethylnaphthalene, 1,7-dimethylnaphthalene and 1,8-dimethylnaphthalene;

(3) the group of 1,4-dimethylnaphthalene: 1,3-dimethylnaphthalene, 1,4-dimethylnaphthalene and 2,3-dimethylnaphthalene; and (4) the group of 1,2-dimethylnaphthalene: 1,2-dimethylnaphthalene.

Various methods for isomerizing a dimethylnaphthalene have been proposed so far: for instance, a method in which a dimethylnaphthalene included in one of the above described four groups is isomerized to one included in the same group by using, as a catalyst, mordenite-type zeolite (e.g., Japanese Patent Laid-Open Publications No. 47020/1980 and No. 298675/1994); and a method in which a dimethylnaphthalene included in the group of 2,6-dimethylnaphthalene is isomerized to one included in this group by using, as a catalyst, faujasite-type zeolite represented by Y-type zeolite (e.g., Publication No. 500052/1991 of Japanese Translation of PCT Patent Application).

Further, a method using a pentasil-type crystalline aluminosilicate catalyst, the entrance of the main cavity of this aluminosilicate being defined by a ten-oxygen-membered ring, has been proposed as a method for isomerizing a dimethylnaphthalene included in the group of 2,7-dimethylnaphthalene to one included in the group of 2,6-dimethylnaphthalene (e.g., Japanese Patent Laid-Open Publication No.88433/1984). There has also been proposed, as a method for isomerizing a dimethylnaphthalene included in the group of 2,3-dimethylnaphthalene to one included in the group of 2,7-dimethylnaphthalene or of 2,6-dimethylnaphthalene, a method in which a pentasil-type crystalline aluminosilicate composed of particles containing 50% by volume or more of such particles whose secondary particles have diameters smaller than 5 μm is used as a catalyst in order to increase the efficiency of isomerization between two dimethylnaphthalenes included in different groups (e.g., Japanese Patent Laid-Open Publication No. 255139/1993).

Furthermore, there is a report on the studies in the relationship between the particle diameters of crystals and catalytic performance, in the correlation between the distribution of acid centers present on the internal or external surfaces of crystals and shape selectivity, and in the shape-selective isomerization of dimethylnaphthalenes ("Effects of Particle Diameters of Crystals of H-ZSM-5 Catalyst on the Isomerization of Dimethylnaphthalenes", 78th CATSJ Meeting Abstracts: Vol. 38, No. 6, 1966, No. 4, B05, 474–477 (1996)). In addition, a process for rapidly producing a zeolite catalyst has been reported (T, Inui, "Mechanism of Rapid Zeolite Crystallization and Its Applications to Catalyst Synthesis", Zeolite Synthesis, ACS Symp. Series, 398, Chapter 33, 1989, American Chemical Society).

With respect to poisoning of zeolite catalysts on the external surfaces of their crystals and in their internal cavities, there is a report on poisoning of HZSM-5 by quinolines on its external surface (S. Namba, et al., Journal of Catalysis, 88, 505–508(1984)).

SUMMARY OF THE INVENTION

We found the following: a metallosilicate catalyst that comprises a metallosilicate having a main cavity defined by a ten-oxygen-membered ring, that is in the form of aggregates of fine crystals of the metallosilicate, the external surface area of the aggregate being in a specific range, and that has been treated to inactivate acid centers present on the external surfaces of the fine crystals until the rate constant basic value becomes a predetermined value shows great reaction specificity and high shape selectivity in various chemical reactions, and achieves high reaction efficiency and high degrees of conversion to remarkably increase the yields of desired products. The present invention.,is based on this finding.

An object of the present invention is therefore to provide a process for producing petrochemicals, using a metallosilicate catalyst that comprises a metallosilicate having a main cavity defined by a ten-oxygen-membered ring and that can increase the activity of various chemical reactions.

One aspect of the present invention is a process for producing 2,6-dimethylnaphthalene by subjecting 2,7-dimethylnaphthalene to an isomerization reaction, wherein the isomerization reaction is carried out by the use of a metallosilicate catalyst that comprises a metallosilicate having a main cavity defined by a ten-oxygen-membered ring, that is in the form of aggregates of fine crystals of the metallosilicate, the external surface area of the aggregate as calculated from t-plot analysis made in the nitrogen adsorption method being 25 $m^2/g$ or more, and that has been treated to inactivate acid centers present on the external surfaces of the fine crystals until the rate constant basic value N becomes 0.5 or less.

DETAILED DESCRIPTION OF THE INVENTION

Metallosilicate Catalyst

The metallosilicate catalyst for use in the present invention is a metallosilicate catalyst that comprises a metallosilicate having a main cavity defined by a ten-oxygen-membered ring, that is in the form of aggregates of fine crystals of the metallosilicate, the external surface area of the aggregate as calculated from t-plot analysis made in the nitrogen adsorption method being 25 $m^2/g$ or more, and that has been treated to inactivate acid centers present on the external surfaces of the fine crystals until the rate constant basic value N becomes 0.5 or less.

The metallosilicate catalyst for use in the present invention shows great reaction specificity and high shape selectivity in various chemical reactions, and can improve reaction activity and production efficiency to increase the yields of desired products. The reason why the metallosilicate catalyst has such advantageous properties has not yet been clarified. However, it is firstly assumed as follows: since aggregates of fine crystals of a metallosilicate, the external surface area of the aggregate as calculated from t-plot analysis made in the nitrogen adsorption method being 25 $m^2/g$ or more are used as the catalyst, the effective surface area of the catalyst that is the entrances of the cavities in the fine crystals, each defined by a ten-oxygen-membered ring is increased; as a result, the cavities in the crystals can effectively be utilized, and the reaction efficiency inside the cavities is thus increased. Further, it is also assumed that, since acid centers present on the external surfaces of the fine crystals are inactivated until the rate constant basic value N becomes 0.5 or less, side reactions do not occur at these acid centers. Therefore, it seems that both the shape selectivity and the reaction efficiency inside the cavities in the crystals are improved because the above two factors are well balanced.

An aluminosilicate or a metallosilicate containing a metal other than aluminum, having a main cavity defined by a ten-oxygen-membered ring can be used as the metallosilicate in the metallosilicate catalyst for use in the present invention. Typical examples of such metallosilicates include aluminosilicates having main cavities defined by ten-oxygen-membered rings, such as ZSM-5 and ZSM-11, and metallosilicates having main cavities defined by ten-oxygen-membered rings, such as ferri(Fe)silicate, gallo(Ga)silicate and boro(B)silicate. These metallosilicates may form a crystal either singly or in combination of two or more members.

The metallosilicate catalyst for use in the present invention is in the form of aggregates of fine crystals of a metallosilicate, the aggregate being composed of fine metallosilicate crystals and moderate voids formed between these fine crystals. The fine crystal of a metallosilicate may be in any shape, for example, in the shape of a fine pillar, a thin layer, a pillar, a layer, a cube or a rectangular parallelepiped. It is preferable that the fine crystal be in the shape of a fine pillar or a thin layer. In the present invention, a fine crystal in any shape can be used, but the length of its short side or its thickness is required to be approximately 0.5 $\mu$m or less, preferably about 0.2 $\mu$m or less, more preferably about 0.1 $\mu$m or less.

These fine crystals aggregate to be an aggregate of secondary, tertiary, or higher-order structure. There is no particular limitation on the size of this aggregate. In general, however, this size is in the range of about 1 to 8 $\mu$m. It is preferable that voids (about 10 nm to about 100 nm) be present between the crystals in the aggregate. However, not all of the fine crystals in the aggregate are separated from one another, and the aggregate as a whole has strength that is generally required for a solid catalyst. For instance, in the case of an aggregate of plate-like crystals, the aggregate is in such a state that a large number of plate-like crystals in different sizes are laminated.

For this reason, in the metallosilicate catalyst for use in the present invention, the external surface area of the aggregate of fine crystals is defined not as the sum total of the external surface areas of the individual fine crystals obtainable by calculation, but as the effective surface area of the aggregate that varies depending upon the state of aggregation of the fine crystals. Specifically, the external surface area of the aggregate of fine crystals is determined by t-plot analysis made in the nitrogen adsorption method. We found that the catalytic activity of the metallosilicate catalyst can be evaluated by the external surface area of the aggregate of fine crystals determined by the nitrogen adsorption method more linearly than by the size of the aggregate or of the fine crystals obtained by calculation from X-ray diffraction analysis, which is used ordinarily.

According to a preferred embodiment of the present invention, it is preferable to use, as the metallosilicate catalyst, aggregates of fine crystals of a metallosilicate, the external surface area of the aggregate as calculated from t-plot analysis made in the nitrogen adsorption method being 25 $m^2/g$ or more, preferably 30 $m^2/g$ or more, more preferably 35 $m^2/g$ or more.

In this specification, the "nitrogen adsorption method" is the conventional nitrogen adsorption method usually used for measuring the specific surface area of a porous material. This method of measurement is a conventional method for measuring a BET surface area, and can be effected in the following manner: a sample that has been dried is placed in a glass-made cell, and deaerated under vacuum; nitrogen gas is introduced into this cell little by little at a temperature of 77° K; and the equilibrium pressure and the amount of nitrogen adsorbed are measured. t-Plot analysis is performed for this porous sample by the use of the adsorption isotherm obtained from the above-described method of measurement.

The "t-plot analysis" is performed to analyze the data obtained from the above-described nitrogen adsorption method. This analysis uses a t-curve that is a standard isotherm obtainable by plotting the thickness t of an adsorption film against relative pressure $p/p_0$ (the t-plot method by Lippens de Boer). Specifically, a t-curve is represented by the following equation (I):

$$t=(V/V_m)\sigma \quad (I)$$

wherein t represents the thickness of an adsorption film, $V/V_m$ represents the average number of adsorption layers contained in the adsorption film, and a represents the thickness of a monomolecular layer.

A t-plot is a plot of the amount v of nitrogen adsorbed versus the thickness t of an adsorption film, and obtainable herein as the t-plot is a straight line bending at the t value that corresponds to the diameter of a pore. From the gradient of this straight line on the higher-pressure side, that is, on the greater-t-value side, the external surface area of the porous sample can be determined. The measurement in accordance with the nitrogen adsorption method, and the analyses of the BET specific surface area and of the external surface area obtained from the t-plot can be made by a commercially available nitrogen adsorption analyzer (e.g., "Bellsorp 28" manufactured by Nippon Bell Kabushiki Kaisha, Japan).

The metallosilicate catalyst for use in the present invention comprises a metallosilicate whose main cavity is defined by a ten-oxygen-membered ring. The "main cavity defined by a ten-oxygen-membered ring" herein means a major cavity among those cavities present in the metallosilicate, having an entrance formed by a ten-oxygen-membered ring. By the "ten-oxygen-membered ring" is herein meant a ring composed of silicon or metallic atoms and oxygen atoms, the number of oxygen atoms constituting the ring being 10. The diameter of the main cavity defined by a ten-oxygen-membered ring is said to be approximately 0.6 nm.

In the present invention, the metallosilicate catalyst that comprises a metallosilicate having a main cavity defined by a ten-oxygen-membered ring and that is in the form of aggregates of fine crystals of the metallosilicate is used after being subjected to such treatment that acid centers present on the external surfaces of the fine crystals are inactivated until the rate constant basic value N becomes 0.5 or less, preferably 0.3 or less, more preferably 0.2 or less.

Typical methods for inactivating acid centers present on the external surfaces of fine crystals, useful in the present invention include the following: a method in which an organic base whose molecular size is larger than the diameter of the main cavity defined by a ten-oxygen-membered ring, for instance,sa quinoline such as dimethylquinoline (e.g., 2,4-dimethylquinoline), trimethylquinoline or β-naphthoquinoline is added, a silica-coating method, for example, a method in which!tetraethyl or tetramethyl silicate is deposited on the metallosilicate catalyst) and the resultant is then subjected to thermal decomposition; a method in which an inorganic base compound (e.g., a compound of Ba, Mg, or the like) is added; a method in which aluminum-removing treatment is conducted by the use of silicon tetrachloride; and any combination of these methods. In a preferred embodiment of the present invention, a method in which a quinoline, especially 2,4-dimethylquinoline, is added, and a silica-coating method are preferred.

An index for inactivation is obtained in the following manner: the reaction of triisopropylbenzene (incapable of entering into the main cavity in the fine crystal, defined by a ten-oxygen-membered ring) or ethylbenzene (capable of entering into the main cavity in the fine crystal, defined by a ten-oxygen-membered ring) is carried out over the metallosilicate catalyst before or after being subjected to the inactivation treatment and in a fixed-bed reactor; and the degree of conversion of the triisopropylbenzene and that of the ethylbenzene are introduced to the following equation (II) to calculate the rate-constant basic value N:

$$N = \frac{[\{-\ln(1-X)\}/\{-\ln(1-X_0)\}]TIPB}{[\{-\ln(1-X)\}/\{-\ln(1-X_0)\}]EB} \quad (II)$$

wherein X represents the degree of conversion in the case where the catalyst after being subjected to the inactivation treatment was used, $X_0$ represents the degree of conversion in the case where the catalyst before being subjected to the inactivation treatment was used, TIPB means triisopropylbenzene, and EB means ethylbenzene.

When this rate constant basic value N is used, the influences of differences in temperature and contact time are eliminated. The degree of inactivation of the catalyst can thus be evaluated objectively as reaction rate ratio.

A preferred method of measurement useful for obtaining the rate constant basic value N by calculation is a method using a fixed-bed reactor which is controlled so that a constant reaction temperature through the bed is realized. For instance, in the case where a fixed-bed reactor having an inner diameter of 0.8 cm is used, the following method of measurement can be employed: 1 g of a metallosilicate catalyst is charged to the isothermal fixed-bed reactor, and triisopropylbenzene or ethylbenzene is fed, at 400° C. under normal pressures, to the fixed-bed reactor at a feed rate of 2.5 g/h while feeding nitrogen as a carrier gas at a feed rate of 1.79 NL/h; after 30 minutes, the oil produced is fully recovered over 15 minutes, and the degree of conversion of the feedstock is obtained with a gas chromatograph.

Process for Producing Metallosilicate

A metallosilicate having a main cavity defined by a ten-oxygen-membered ring, which is an essential component of the metallosilicate catalyst for use in the present invention, can be produced in accordance with the process described below in detail.

In one embodiment of the present invention, ZSM-5, one aluminosilicate having a main cavity defined by a ten-oxygen-membered ring, can be produced by heating, to 100–175° C. in an autoclave, a gelled mixture of starting compounds whose compositions are in the ranges shown in Table 1 (see "Zeoraito no Kagaku to Oyo (Science and Applications of Zeolite)", edited by Hiroo Tominaga, page 87, Kodansha Scientific, Japan (1987)).

TABLE 1

| | |
|---|---|
| $SiO_2/Al_2O_3$ | 20 – 60, preferably 25 – 35 |
| $Na_2O/Al_2O_3$ | ≧1, preferably 1 – 2 |
| $(TPA)_2O/Al_2O_3$ | ≧1, preferably 1 – 10 |
| $H_2O/(Na_2O + (TPA)_2O)$ | 5 – 50, preferably 20 – 40 |

TPA: tetrapropyl ammonium ion

According to a preferred embodiment of the present invention, the metallosilicate catalyst for use in the present invention can be synthesized in accordance with the "rapid crystallization method" described in the literature by T, Inui ("Mechanism of Rapid Zeolite Crystallization and Its Applications to Catalyst Synthesis", chapter 33, 1989, American Chemical Society). By this rapid crystallization method, aggregates of fine crystals of a metallosilicate having a main cavity defined by a ten-oxygen-membered ring, the external surface area of the aggregate being large can be produced in a shorter time than by other production methods. Further, as compared with metallosilicates produced by other methods, a metallosilicate produced by this method has a small number of acid centers on the external surface of its crystal, and the activity of this external surface is also low. The outline of the "rapid crystallization method" is as follows.

Liquids A and B having the compositions shown in Table 2 are added to liquid C to form a gel while maintaining the pH of the mixture at 9–11, and this gel is subjected to centrifugal separation. The precipitate is taken out, ground in a mortar, and subjected again to centrifugal separation. This operation is repeated two or three times, and the precipitate (D) is recovered. Separately, liquids A' and B' having the compositions shown in Table 3 are added to liquid C' to form a gel. This gel is centrifuged, and the supernatant liquid (E) is recovered. The precipitate D is added to this supernatant liquid E, and the mixture is placed in an autoclave. The temperature of the mixture is raised from normal temperatures to 1600° C. at an average heat-up rate of 1° C./min, and from 160 to 210° C. at a heat-up rate of approximately 0.2° C./min. After maintaining at 210° C. for 25 minutes, the mixture is cooled, and filtered. The crystals collected are washed with water, dried, and then calcined to yield ZSM-5, a metallosilicate according to the present invention, having a main cavity defined by a ten-oxygen-membered ring; this is in the form of aggregates of the crystals of the metallosilicate, the external surface area of the aggregate being in a specific range. In this method, aluminum nitrate can be used instead of aluminum sulfate as a source of aluminum. The source of aluminum is used in an amount calculated from the Si/Al ratio in ZSM-5 to be produced. It is also possible to produce ferrisilicate by using, in this "rapid crystallization method", a source of iron (e.g., iron nitrate) instead of the source of aluminum.

TABLE 2

| Liquid A (Solution containing a source of Al): | aluminum sulfate, $H_2SO_4$, water, NaCl, TPAB (tetrapropyl ammonium bromide) |
|---|---|
| Liquid B (Solution containing a source of Si): | water glass (sodium silicate), water |
| Liquid C: | NaCl, NaOH, $H_2SO_4$, water, TPAB |

NaCl and TPAB used in liquid A may be used in liquid C.

TABLE 3

| Liquid A' (Solution containing a source of Al): | aluminum sulfate, $H_2SO_4$, water, TPAB |
|---|---|
| Liquid B' (Solution containing a source of Si): | water glass (sodium silicate), water |
| Liquid C': | NaCl, water |

TPAB used in liquid A' may be used in liquid C'.

By inactivating acid centers present on the external surfaces of the above-obtained fine crystals of the metallosilicate until the rate constant basic value falls in a specific range, it is possible to make the metallosilicate into a metallosilicate catalyst according to the present invention. The metallosilicate catalyst according to the present invention, comprising the metallosilicate having a main cavity defined by a ten-oxygen-membered ring may be subjected to proper treatment before it is used for various chemical reactions. In a preferred embodiment of the present invention, the metallosilicate catalyst according to the present invention may be used after it is ion-exchanged to proton type. The ion exchange of the catalyst to proton type can be effected by the use of, for instance, an aqueous solution of ammonium chloride.

Process for Producing 2.6-Dimethylnaphthalene (Isomerization Reaction)

In this production process of the present invention, not only 2,7-dimethylnaphthalene itself but also stock oil containing 2,7-dimethyl-naphthalene in a significant amount can be used as feedstock. It is also possible to use 2,7-dimethylnaphthalene produced by the process for producing a dialkylnaphthalene according to the present invention, which will be described later in detail.

In this production process of the invention, an isomerization reaction is carried out. This reaction is characterized by using, as a catalyst, a metallosilicate catalyst according to the present invention, comprising a metallosilicate having a main cavity defined by a ten-oxygen-membered ring.

The reaction temperature in this production process is preferably between 200° C. and 500° C., more preferably between 250° C. and 450° C. When the isomerization reaction is carried out at a temperature of 200° C. or higher, the reaction proceeds thoroughly, and 2,6-dimethylnaphthalene is produced in an increased yield. When the reaction is carried out at a temperature of 500° C. or lower, undesirable side reactions do not occur. Moreover, it is not necessary to install heat-resistant equipment suitable for high-temperature reactions, so that such a reaction temperature is favorable also from an economical point of view.

In this production process, the reaction is carried out at a pressure preferably between normal pressures and 50 $kg/cm^2$, more preferably between normal pressures and 30 $kg/cm^2$. By carrying out the reaction at a pressure of 50 $kg/cm^2$ or lower, it is possible to decrease the power required for compression systems. Moreover, it is unnecessary to install high-pressure equipment. Such a pressure is thus favorable also from an economical point of view.

Any reactor of fixed, moving or fluidized bed type can be used in this production process of the invention.

From the product produced by this production process, 2,6-dimethylnaphthalene is isolated and recovered. The isolation/recovery step can be conducted, for example, through a conventional distillation, adsorption or crystallization operation, or a combination thereof.

Process for Producing Dialkylnaphthalene

In this production process of the invention, it is possible to use, as feedstock, not only methylnaphthalene, naphthalene or a mixture of these compounds, but also stock oil containing methylnaphthalene and/or naphthalene in a significant amount. For example, there may be used methylnaphthalene (preferably β-methylnaphthalene) or naphthalene produced by the process for producing methylnaphthalene or naphthalene according to the present invention, which will be described later in detail.

In this production process of the invention, an alkylation or transalkylation reaction is carried out. These reactions are characterized by using, as a catalyst, a metallosilicate catalyst of the present invention, comprising a metallosilicate having a main cavity defined by a ten-oxygen-membered ring.

In this production process, an alkylation or transalkylation agent is used. Typical examples of alkylation or transalkylation agents include arenes, alkenes, alcohols, esters, ethers and alkyl halides. Preferable alkylation or transalkylation agents are as follows.

Typical examples of arenes include arenes containing at least one alkyl group having not more than 5 carbon atoms. Preferable arenes are alkylbenzenes and/or alkylnaphthalenes containing at least one alkyl group having not more than 2 carbon atoms.

Preferable examples of alkenes are alkenes having not more than 5 carbon atoms; and ethylene is more preferred.

Typical examples of alcohols include alcohols containing at least one alkyl group having not more than 5 carbon atoms. Primary alcohols having at least either methyl or ethyl group are preferred, and methyl or ethyl alcohol is more preferred.

Typical examples of esters or ethers include those ones containing at least one alkyl group having not more than 5 carbon atoms. Esters or ethers having at least either methyl or ethyl group are preferred, and dimethyl carbonate is more preferred.

The reaction temperature in this production process is preferably from 200 to 550° C., more preferably from 250 to 490° C. When the alkylation or transalkylation reaction is carried out at a temperature of 200° C. or higher, the reaction proceeds thoroughly, and a dialkylnaphthalene is produced in an increased yield. When the reaction is carried out at a temperature of 550° C. or lower, the reaction never proceeds excessively, so that unfavorable side reactions do not occur. Moreover, it is not necessary to install heat-resistant equipment suitable for high-temperature reactions. Therefore, such a reaction temperature is favorable also from an economical point of view.

To particularly increase the yields of 2,6-dialkylnaphthalenes, it is necessary to properly establish temperature conditions. By making the temperature conditions proper, it is possible to carry out the alkylation or transalkylation reaction without causing side reactions.

In this production process, the reaction is carried out at a pressure preferably between normal pressures and 50 $kg/cm^2$, more preferably between normal pressures and 30 $kg/cm^2$. By carrying out the reaction at a pressure of 50 $kg/cm^2$ or lower, it is possible to decrease the power required for compression systems. Moreover, it is not necessary to install high-pressure equipment. Such a reaction pressure is thus favorable also from an economical point of view.

Any reactor that can be used in the aforementioned process for producing 2,6-dimethylnaphthalene can be used in this production process of the invention.

From the product produced by this production process, a dialkylnaphthalene (preferably dimethylnaphthalene) is isolated and recovered. The isolation/recovery step can be conducted through a conventional distillation operation or the like.

Process for Producing 2,6-Dimethylnaphthalene

According to one embodiment of the present invention, 2,6-dimethylnaphthalene can be produced, starting from methylnaphthalene or naphthalene, by using the aforementioned process for producing a dialkylnaphthalene and the previously described process for producing 2,6-dimethylnaphthalene (isomerization reaction) in combination. Those catalysts, reaction conditions and reactors that are suitable for these two production processes can be used in this production process.

According to a preferred embodiment of the present invention, 2,6-dimethylnaphthalene can be produced by the combination use of the process for producing methylnaphthalene or naphthalene by subjecting an alkylnaphthalene to a hydrodealkylation reaction, which will be described later in detail, the above-described process for producing a dialkylnaphthalene, and the previously described process for producing 2,6-dimethylnaphthalene (isomerization reaction). Those catalysts, reaction conditions and reactors that are suitable for these three production processes can be used in this production process.

Process for Producing Methylnaphthalene or Naphthalene

Not only an alkylnaphthalene itself but also stock oil containing an alkylnaphthalene in a significant amount can be used as feedstock in this process. Typical examples of useful feedstock include a fraction of cracked or reformed oil of petroleum refining and/or petroleum refining products, for example, cracked or reformed distillates obtained from the catalytic cracking, thermal cracking or catalytic reforming of petroleum, or from a process for producing ethylene from petroleum; coal tar distillate; liquefied coal oil; and mixtures thereof. of the above-described cracked or reformed oil fractions of petroleum and/or refined petroleum products, those fractions having boiling points of 170 to 300° C., more preferably 210 to 280° C. are preferred as the stock oil for use in this production process of the present invention. More preferable stock oil is a cracked gas oil fraction having boiling points of 210 to 280° C. obtained from the catalytic cracking of petroleum.

The stock oil can contain such impurities as sulfur-containing compounds, for example, benzothiophenes, nitrogen-containing compounds for example, quinolines and indoles, and oxygen-containing compounds, for example, phenols, benzofuran and dibenzofuran.

In this production process of the invention, a hydrodealkylation reaction is carried out. For this reaction, zeolite or a zeolite composition, for example, a catalyst for the fluid catalytic cracking (FCC) of petroleum, can be used as a catalyst. It is also possible to use such a catalyst that an active metallic component, and, if necessary, optional components are supported on a porous body having porous structure.

Any of metals such as vanadium (V), molybdenum (Mo), chromium (Cr), cobalt (Co), nickel (Ni), platinum (Pt), rhodium (Rh) and iridium (Ir), oxides or sulfides of these metals, and mixtures thereof can be used as the active metallic component.

The concentration of the active metallic component, calculated in terms of metal is preferably from 0.1 to 30% by weight, more preferably from 0.2 to 15% by weight.

Alumina, silica, silica alumina, kaolin, or a combination thereof is used as the porous body having porous structure. Particularly preferred are kaolin and alumina. Zeolite can be incorporated into this carrier to further increase the dealkylation activity.

The mean diameter of pores in the porous body having porous structure is preferably from 70 to 800 angstroms, more preferably from 80 to 700 angstroms.

Alkali metals, alkali earth metals, rare earth elements or the like may be used as the optional components in order to increase the heat resistance and selectivity of the catalyst.

A preferable catalyst for the hydrodealkylation reaction in the present invention is one whose active metallic component is vanadium (V) oxide or sulfide and whose carrier that supports the active metallic component is a porous body having porous structure, capable of fulfilling the above described requirements. Such a catalyst shows excellent desulfurizing activity even when coke is deposited on the catalyst.

The reaction temperature in this production process of the invention is preferably from 450 to 700° C., more preferably from 500 to 670° C. By carrying out the reaction at a temperature of 450° C. or higher, it is possible to make the degrees of dealkylation and desulfurization higher, so that methylnaphthalene having improved quality can be obtained in an increased yield. When the hydrodealkylation reaction is carried out at a temperature of 700° C. or lower, the reaction never proceeds excessively, and unfavorable side reactions do not take place. Moreover, investment in plant and equipment such as heat-resistant equipment suitable for high-temperature reactions is not required as long as the reaction is carried out at such a temperature.

When the hydrodealkylation reaction is carried out in this production process of the invention, the partial pressure of hydrogen is controlled to preferably $1 \geq 50$ $kg/cm^2$, more preferably 3–30 $kg/cm^2$. By controlling the partial pressure of hydrogen to 1 kg/cm$^2$ or higher, it is possible to make the degrees of hydrodealkylation and desulfurization higher, and to prevent the deposition of coke on the surface of the catalyst. By controlling the partial pressure of hydrogen to 50 kg/cm$^2$ or lower, it is possible to prevent hydrocracking reaction that is induced by the hydrogenation of naphthalene ring. As a result, the reaction selectivity is increased, and the consumption of hydrogen is thus reduced.

In this production process of the invention, the contact time is preferably from 1 to 35 seconds, more preferably from 2 to 30 seconds. By making the contact time 1 second or longer, it is possible to attain higher degrees of dealkylation and desulfurization. By making the contact time 35 seconds or shorter, it is possible to prevent excessive progress of the dealkylation reaction. Moreover, it is not necessary to make the reactor larger, so that such a contact time requires less economical burden.

From the product produced by this production process of the invention, naphthalene, methylnaphthalene (preferably β-methylnaphthalene), or a mixture thereof is isolated and recovered. The isolation/recovery step can be conducted through a conventional distillation operation or the like.

Any reactor of fixed, moving or fluidized bed type can be used for this production process of the invention. A reactor of fluidized bed type is particularly preferred. The reason for this is as follows: the thermal conductivity of such a reactor is high, and the temperature of the reaction system is thus maintained constant, so that even a reaction accompanying large heat of reaction, such as a hydrodealkylation reaction, proceeds smoothly; in addition, it is possible to continuously conduct both the removal of a degraded catalyst and the feeding of a regenerated or fresh catalyst.

A desirable fluidized-bed reactor is one having a plurality of fluidized beds composed of a reactor and a regenerator, a catalyst being circulated between these fluidized beds. A fluidized-bed reactor may be of any type such as dense phase type or riser type.

EXAMPLES

Preparation of Metallosilicate Catalyst

By the use of liquids for preparing a gel and those for preparing mother liquor, the compositions of these liquids being shown in Table 4, ZSM-5 (Si/Al=20) was synthesized in accordance with the "rapid crystallization method".

To stirred liquid C in a beaker, liquids A and B were respectively fed with the aid of a microtube pump while maintaining the pH of the mixture at 9–10. The gelled mixture produced was centrifuged, and the supernatant liquid was removed. The residue was ground in an automatic mortar for 30 minutes, and subjected to centrifugal separation again. After removing the supernatant liquid, the residue was ground in an automatic mortar for 30 minutes, and then centrifuged to obtain a gelled precipitate. Each centrifugal separation was conducted at 2,000 rpm for 5 minutes.

A gelled mixture was obtained from liquids A', B' and C' in the same manner as the above, and subjected to centrifugal separation. The supernatant liquid obtained was used as mother liquor.

The gelled precipitate and the mother liquor were mixed, and the mixture was placed in a Teflon container. This container was then placed in an autoclave, and the mixture was stirred to conduct hydrothermal synthesis. The temperature of the mixture was raised from normal temperatures to 160° C. at an average heat-up rate of 1° C./min, and from 160 to 210° C. at a heat-up rate of 0.2° C./min. The mixture was maintained at 210° C. for 25 minutes, and then cooled. The stirring of the mixture in the autoclave was conducted with a stirrer equipped with a propeller-type impeller having three propeller blades, manufactured by Sunplatech Corporation.

The contents of the Teflon container were taken out, and subjected to centrifugal separation. The supernatant liquid was removed. The residue was washed with pure water until the pH of the washing water used became 8, and then subjected to centrifugal separation. The precipitate was dried at 110° C., and calcined at 540° C. for 3.5 hours to yield 18.7 g of ZSM-5.

This ZSM-5 was placed in 0.94 litters of a 1 N aqueous solution of NH$_4$NO$_3$ at 800° C., and the mixture was stirred for 1 hour. The mixture was then subjected to centrifugal separation, and the supernatant liquid was removed. This operation was repeated twice. Thereafter, the residue was placed in pure water, and the mixture was stirred. The mixture was subjected to centrifugal separation, and the supernatant liquid was removed. This operation was repeated 5 times. Subsequently, the residue was dried in an electric oven at 110° C. for 3 hours, followed by calcination at 540° C. for 3.5 hours, thereby obtaining ZSM-5 of proton type.

TABLE 4

| | For the preparation of gel | |
|---|---|---|
| Liquid A | aluminum nitrate nonahydrate | 6.25 g |
| | H$_2$SO$_4$ | 6.19 g |
| | H$_2$O | 60 g |
| Liquid B | sodium silicate | 69 g |
| | (SiO$_2$ = 28 – 30 wt %) | |
| | H$_2$O | 45 g |
| Liquid C | NaCl | 52.5 g |
| | NaOH | 2.39 g |
| | H$_2$SO$_4$ | 2.84 g |
| | H$_2$O | 208 g |
| | TPAB | 7.91 g |
| | For the preparation of mother liquor | |
| Liquid A' | aluminum nitrate nonahydrate | 6.25 g |
| | H$_2$SO$_4$ | 6.19 g |
| | H$_2$O | 60 g |
| Liquid B' | sodium silicate | 69 g |
| | (SiO$_2$ = 28 – 30 wt %) | |
| | H$_2$O | 45 g |
| Liquid C' | NaCl | 26.3 g |
| | H$_2$O | 104 g |
| | TPAB | 7.53 g |

When the hydrothermal synthesis was conducted in the above-described production process, the mixture placed in the autoclave was stirred at a rate of 60–80 rpm or of 200 rpm. The 5 catalyst produced under the former stirring condition is referred to as ZSM-5 of Example 1, and the one produced under the latter stirring condition is referred to as ZSM-5 of Example 2. H-ZSM-5 manufactured by NE Chemcat Kabushiki Kaisha, Japan is referred to as a catalyst of Comparative Example. The physical properties of the metallosilicate catalysts of Examples 1 and 2, and those of the catalyst of Comparative Example were as shown in Tables 5 and 6.

TABLE 5

| | BET Surface Area m$^2$/g | t-Plot External Surface Area m$^2$/g | Alc % | Als % | Als/Alc |
|---|---|---|---|---|---|
| Example 1 | 426 | 39.2 | 5.46 | 6.58 | 1.21 |
| Example 2 | 442 | 52.8 | 4.58 | 5.48 | 1.20 |
| Comparative Example | 426 | 19.0 | 3.29 | 4.58 | 1.39 |

In the above table, "Alc" represents the proportion (%) of the number of Al atoms to the total number of Al atoms and Si atoms, Al/(Al+Si), calculated from the Al concentration and the Si concentration in the whole crystals that are determined by ICP emission spectroscopic analysis; and "Als" represents the proportion (%) Al/(Al+Si) calculated from the Al concentration and the Si concentration on the external surfaces of the crystals that are determined by ESCA analysis.

TABLE 6

| | Size of Crystals Determined by XRD (nm) | Shapes of Crystals Observed by SEM |
|---|---|---|
| Example 1 | 48 nm | fine pillar, thin layers laminated |
| Example 2 | 40 nm | thin layers laminated |
| Comparative Example | 43 nm | fine pillars fused, hexagonal prism |

EVALUATION TESTS

Evaluation Test 1

The metallosilicate catalysts were evaluated in terms of converting property and selectivity. This evaluation was conducted in accordance with the following methods of reaction and calculation.

Used herein was a fixed-bed reactor made of a stainless steel cylinder whose inner diameter was 0.8 cm, having an inlet for feedstock and an outlet for a reaction product. To make the temperature of the entire reactor uniform, this reactor was placed in a sand-fluidized bath having a built-in heater. One gram of the metallosilicate catalyst of Example 1 or 2 or that of Comparative Example was placed at the central part of this reactor, and fixed to it with woolly quartz.

Reaction was carried out by feeding stock oil that was a 1:5 (weight basis) mixture of 2,7-dimethylnaphthalene, feedstock, and 1,3, 5-trimethyl-benzene, solvent, and nitrogen, carrier gas, to the reactor from the inlet at feed rates of 2.5 g/h and 1.79 NL/h, respectively. The reaction conditions were as follows: the pressure was normal pressures; the reaction temperature was 300° C., 400° C. or 500° C.; and the reaction time was 3 to 40 hours. The oil produced was condensed at a cooling section connected to the outlet of the reactor, and recovered every 1 hour.

The oil produced was analyzed by a gas chromatograph model "GC5890" manufactured by YOKOGAWA HEWLETT PACKARD, LTD., Japan, wherein a PLC column manufactured by Shinwa Kako Kabushiki Kaisha, Japan was used to analyze the oil for dimethylnaphthalene isomers, and a non-polar DB-1 column, for components other than these isomers.

To evaluate the metallosilicates of Examples 1 and 2, and that of Comparative Example, degree of conversion, selectivity and yield were respectively calculated by using the following equations.

Degree of conversion (%) ={(the total concentration of all naphthalenes in the oil produced−the concentration of 2,7-dimethylnaphthalene in the oil produced)/the total concentration of all naphthalenes in the oil produced}×100

Selectivity (%) {the concentration of 2,6-dimethylnaphthalene in the oil produced/(the total concentration of all naphthalenes in the oil produced−the concentration of 2,7-dimethylnaphthalene in the oil produced)}×100

Yield (%)=degree of conversion×selectivity÷100

The results were as shown in the following Table 7.

TABLE 7

| | | 300° C. (0–3 h) | | | 400° C. (0–3 h) | | |
|---|---|---|---|---|---|---|---|
| | t. plot value m²/g | Degree of Conversion (%) | Selectivity (%) | Yield (%) | Degree of Conversion (%) | Selectivity (%) | Yield (%) |
| Example 1 | 39.2 | 44.9 | 14.7 | 6.6 | 64.5 | 32.0 | 20.6 |
| Example 2 | 52.8 | 49.7 | 16.1 | 8.0 | 72.8 | 26.0 | 18.9 |
| Comparative Example | 19.0 | 27.1 | 12.5 | 3.4 | 64.8 | 22.7 | 14.7 |

In Table 7, "Selectivity" is the selectivity for 2,6-dimethyl-naphthalene, and "Yield" is the yield of 2,6-dimethylnaphthalene.

Evaluation Test 2

The durability of the metallosilicate catalyst according to the present invention was tested.

This test was conducted by using the same reaction conditions, and methods of evaluation and calculation as those in Evaluation Test 1, provided that the metallosilicate catalyst of Example 2 was used for the reaction and that the reaction was carried out at 400° C. for many hours.

The results were as shown in the following Table 8.

TABLE 8

| | 400° C. | | |
|---|---|---|---|
| Time (h) | Degree of Conversion (%) | Selectivity (%) | Yield (%) |
| 2 – 3 | 62.2 | 32.8 | 20.4 |
| 8 – 9 | 49.8 | 23.7 | 11.8 |
| 16 – 17 | 41.5 | 31.0 | 12.9 |
| 39 – 40 | 32.2 | 33.5 | 10.8 |

Evaluation Test 3

The converting property and selectivity of the metallosilicate according to the present invention were evaluated.

This evaluation was made by the use of the metallosilicate catalyst of Example 2 after subjecting it to treatment with 2,4-dimethylquinoline to inactivate acid centers present on the external surfaces of the crystals of the metallosilicate, or after subjecting it to silica-coating treatment using tetraethyl silicate to inactivate the acid centers, or without subjecting it to any treatment. In the treatment with 2,4-dimethylquinoline, 2,4-dimethylquinoline was used in an amount of 0.02 to 1.5% by weight of 2,7-dimethylnaphthalene contained in the stock oil. The silica-coating treatment was conducted by introducing tetraethyl silicate vapor to the metallosilicate catalyst, and heating stepwise the catalyst to 500° C.

Reaction was conducted in the same manner as in Evaluation Test 1 except that the metallosilicate catalyst of Example 2 subjected to either one of the above-described treatments or non-treated one was used, that ethylbenzene and triisopropylbenzene were used as the feedstock and that the reaction temperature, the feed rate of the feedstock, and the reaction time were changed to 400° C., 2.5 g/h and 15 minutes, respectively.

The results are shown in Table 9 together with the rate constant basic values N.

When the selectivity becomes high, the degree of conversion itself becomes low because it is strongly affected by the degree of equilibrium conversion (50%) between two components of 2,7-dimethylnaphthalene and 2,6-dimethylnaphthalene (the selectivity for 2,6-dimethylnaphthalene is 100%). Therefore, the degree of relative conversion defined by the following equations with the degree of equilibrium conversion taken into consideration was obtained by calculation, and is shown in Table 9. The degree of relative conversion (%) means the practical degree of conversion in the case where the reaction system is strongly affected by equilibrium, that is, when the selectivity for 2,6-dimethylnaphthalene is high.

Degree of Equilibrium Conversion (%) =100 −(selectivity (%) for 2,6-dimethylnaphthalene)/100×50

Degree of Relative Conversion =(degree of conversion (%)/degree of equilibrium conversion (%))×100

TABLE 9

| N | Degree of Conversion (%) | Degree of Relative Conversion (%) | Selectivity (%) | Treatment of Acid Centers Present on External Surfaces of Crystals |
|---|---|---|---|---|
| 1.0 | 69.5 | 80.0 | 26.2 | None |
| 0.83 | 65.5 | 75.7 | 27.0 | A |
| 0.59 | 55.8 | 64.3 | 26.4 | B |
| 0.45 | 52.5 | 61.4 | 29.0 | A |
| 0.32 | 50.0 | 59.2 | 31.0 | A |
| 0.21 | 38.2 | 47.8 | 40.2 | A |
| 0.10 | 34.7 | 47.7 | 54.4 | B |
| 0.072 | 32.4 | 45.5 | 57.5 | A |
| 0.047 | 34.5 | 59.1 | 83.3 | A |

In Table 9, "A" denotes that the catalyst that had been treated with 2,4-dimethylquinoline was used, and "B" denotes that the catalyst that had been subjected to the silica-coating treatment using tetraethyl silicate was used.

What is claimed is:

1. A process for producing 2,6-dimethylnaphthalene by subjecting 2,7-dimethylnaphthalene to an isomerization reaction, wherein the isomerization reaction is carried out by the use of a metallosilicate catalyst that comprises a metallosilicate having a main cavity defined by a ten-oxygen-membered ring, the catalyst is in the form of aggregates of fine crystals of the metallosilicate, the external surface area of the aggregate as calculated from t-plot analysis made in the nitrogen adsorption method being 25 $m^2/g$ or more, and the catalyst has been treated to inactivate acid centers present on the external surfaces of the fine crystals until the rate constant basic value N of the catalyst becomes 0.5 or less.

2. A process according to claim 1, using a metallosilicate catalyst produced by a process comprising:

producing aggregates of fine crystals of a metallosilicate having a main cavity defined by a ten-oxygen-membered ring so that the external surface area of the aggregate as calculated from t-plot analysis made in the nitrogen adsorption method will be 25 $m^2/g$ or more, and treating the aggregates to inactivate acid centers present on the external surfaces of the fine crystals until the rate constant basic value N of the catalyst becomes 0.5 or less.

3. The process according to claim 2, wherein the treatment for inactivating the acid centers is conducted by one of the following methods: a method in which an organic base having a molecular size larger than the diameter of the main cavity in the metallosilicate, defined by a ten-oxygen-membered ring is added; a silica-coating method; a method in which an inorganic base compound is added; a method using silicon tetrachloride; or any combination of these methods.

* * * * *